United States Patent [19]

Krivi et al.

[11] Patent Number: 5,130,422
[45] Date of Patent: Jul. 14, 1992

[54] VARIANT SOMATOTROPIN-ENCODING DNA

[75] Inventors: Gwen G. Krivi; Michael R. Schlittler, both of St. Louis; Bernard N. Violand, Glencoe, all of Mo.

[73] Assignee: Monsanto Company, St. Louis, Mo.

[21] Appl. No.: 743,623

[22] Filed: Aug. 12, 1991

Related U.S. Application Data

[62] Division of Ser. No. 237,358, Aug. 29, 1988, Pat. No. 5,089,473.

[51] Int. Cl.$^5$ .................. C07H 15/12; A01N 43/04
[52] U.S. Cl. ...................... 536/27; 435/694; 436/87; 436/817; 530/399; 514/21; 514/44
[58] Field of Search ............... 435/69.4; 436/87, 817; 536/27; 530/350, 399; 514/21, 44

[56] References Cited

U.S. PATENT DOCUMENTS

| | | | |
|---|---|---|---|
| 4,634,677 | 1/1987 | Goeddel et al. | 435/317 |
| 5,037,806 | 8/1991 | Krivi | 514/12 |
| 5,089,473 | 2/1992 | Krivi et al. | 514/12 |

OTHER PUBLICATIONS

Abdel-Meguid et al., Proc. Natl. Acad. Sci, U.S.A., vol. 84, Sep. 1987, pp. 6434–6437.
Seeburg et al, DNA, vol. 2, No. 1, 1983, pp. 37–45.

*Primary Examiner*—David L. Lacey
*Assistant Examiner*—Laurie A. Scheiner
*Attorney, Agent, or Firm*—Wayne R. Eberhardt; Carol H. Clayman; Larry R. Swaney

[57] ABSTRACT

Variant somatotropins are described in which the asparagine located in the 95-101 region are replaced by glutamine which somatotropins exhibits enhanced stability.

11 Claims, No Drawings

VARIANT SOMATOTROPIN-ENCODING DNA

This is a division of application Ser. No. 07/237,358, filed Aug. 29, 1988, now U.S. Pat. No. 5,089,473.

This invention relates to somatotropins (growth hormones), and, more particularly, to variants of somatotropins with enhanced stability.

BACKGROUND OF THE INVENTION

Somatotropins are proteins produced by animals which because of their effect on animal growth are commonly referred to as "growth hormones". Historically, growth hormones (somatotropins) were recovered and purified from pituitary gland extracts. With the advent of recombinant DNA technology, somatotropins can now be produced in quantity free of other proteins of natural origins.

Somatotropins produced by recombinant DNA technology in bacteria are commonly accumulated in insoluble refractile bodies in the cytoplasm of the host cell. To recover the somatotropin in its active form requires renaturation which entails solubilization, folding and oxidation of the protein to its native configuration. Examples of renaturation processes are described in detail in European Patent Applications Publication Numbers 114,506A and 192,629A. These processes and subsequent purification processes are usually carried out at high pH. Somatotropins are unstable under these conditions resulting in yield losses, especially when held for prolonged periods of time. Degradation is also temperature dependent with room temperature being worse than 4° C. (the normal temperature used for processing), however, if there were no stability problem, room temperature operation would be better from the processing viewpoint.

It has now been found that the two major decomposition products of somatotropin under these conditions are (1) an isoform of somatotropin with a beta-linked aspartic acid formed from an asparagine located about midway of the protein chain (positions 95-101), and (2) a two chain form of the molecule caused by a break in the polypeptide chain occurring at the asparagine located about midway of the protein chain, i.e. positions 95-101. The break results from the asparagine being converted to a succinimidyl moiety. These forms are often removed during processing resulting in yield loss.

SUMMARY OF THE INVENTION

It has now been discovered that variant forms of mammalian somatotropins, in which the asparagine located between positions 95-101 has been replaced by glutamine, exhibit enhanced stability at high pH and at elevated temperature while retaining bioactivity equivalent to the corresponding unmutated somatotropins. Any mammalian somatotropin may be mutated in accordance with this invention by replacing the asparagine located in the 95-101 region by glutamine. Any mammalian somatotropin having essentially homologous amino acid sequences in the 95-101 region may be stabilized by converting the asparagine to glutamine in this region. Examples of suitable somatotropins are human somatotropin, bovine somatotropin, porcine somatotropin, ovine somatotropin, equine somatotropin, rat somatotropin and monkey somatotropin.

DETAILED DESCRIPTION OF THE INVENTION

Any mammalian somatotropin is suitable for the practice of this invention because of the recognized homology of mammalian somatotropins. For examples of known somatotropin amino acid sequences see European Patent Application No. 192,629, filed Aug. 27, 1986, Seeberg et al., *DNA* Vol. 2, No. 1, p. 37-45, 1983, and Abdel-Meguid et al., *Proc. Natl. Acad. Sci., USA*, vol. 84, pp. 6434-6437, Sept. 1987, which sequences are incorporated herein by reference. Preferred somatotropins of this invention are bovine and porcine somatotropins.

Illustrative examples of the amino acid sequences of the targeted region of the variant somatotropins of this invention are shown in Table 1. The underlined glutamines are asparagines in the unmutated somatotropins. The numbers represent the amino acid positions counting from the amino terminus of the protein with amino acid in the number one position of the illustrated hormones being phenylalanine. The abbreviations stand for bovine somatotropin (BGH); porcine somatotropin (PGH); ovine somatotropin (OGH); equine somatotropin (EGH); rat somatotropin (RGH); human somatotropin (HGH); and monkey somatotropin (MGH).

TABLE 1

| | Amino Acid Sequences of Targeted Region | | | | | | |
|---|---|---|---|---|---|---|---|
| | 95 | 96 | 97 | 98 | 99 | 100 | 101 |
| BGH | Val | Phe | Thr | Gln | Ser | Leu | Val |
| PGH | Val | Phe | Thr | Gln | Ser | Leu | Val |
| OGH | Val | Phe | Thr | Gln | Ser | Leu | Val |
| EGH | Val | Phe | Thr | Gln | Ser | Leu | Val |
| RGH | Ile | Phe | Thr | Gln | Ser | Leu | Met |
| HGH | Ser | Val | Phe | Ala | Gln | Ser | Leu |
| MGH | Ser | Val | Phe | Ala | Gln | Ser | Leu |

The variants of this invention, i.e. proteins, having the asparagine changed to glutamine in the 95-101 region, are not limited to native somatotropins but include analogues, mutants (e.g. somatotropins containing altered amino acids at other than the asparagine in the 95-101 region) allelic forms, an other variants including extensions and deletions of somatotropins which variants will exhibit the bioactivity of somatotropin and in addition will exhibit enhanced stability at high pH and temperature imparted by the mutation of this invention. For example, satisfactory variants include allelic forms of BGH and PGH in which leucine 126 is replaced by valine.

The somatotropins of this invention may be prepared by chemical synthesis. However, owing to the large size of the somatotropin molecule, it is preferred to prepare them by recombinant DNA technology. This can be done by conventional means by constructing a gene encoding the desired variant somatotropin having glutamine instead of asparagine in the 95-101 region. A convenient way of constructing the variant somatotropin gene is by conventional oligonucleotide-directed site-specific mutagenesis of the starting gene. The mutated gene is then cloned into an appropriate vector which vector subsequently is used to transform a suitable expression host, such as, bacteria (e.g. *E. coli* or Pseudomonas), yeast (e.g. *S. cerevisae*), or mammalian cells (e.g. C127 or CHO). The variant somatotropin is then expressed and recovered in the conventional manner.

One embodiment of the invention is directed to novel DNA sequences coding for mammalian somatotropins in which the codon for asparagine located between positions 95-101 of a native mammalian somatotropin is replaced by a codon for glutamine, i.e. CAA or CAG. The DNA sequences are prepared by conventional chemical or enzymatic means, for example, by synthesis via a gene machine or by oligonucleotide-directed site-specific mutagenesis of a somatotropin gene.

Another embodiment of the invention is a method for enhancing the growth of mammals, preferably beef cattle and pigs, which method comprises treatment of a mammal with an effective amount of a mammalian somatotropin of this invention.

Another embodiment of the invention is a method for increasing milk production in female mammals, such as brood sows and preferably dairy cows, which method comprises the administration of an effective amount of somatotropin of this invention.

The somatotropins of this invention exhibit essentially the same efficacy as the corresponding asparagine containing somatotropins. Accordingly, an effective dose and mode of administration for the somatotropins of this invention are similar to those used for known growth hormones. However, in practice it is preferred to use endogenous somatotropin for treatment of the source species of mammals.

Generally, the effective dosage range is between 1 to 200 milligrams per animal per day. Efficacy varies depending upon the size and maturity of the animal and the amount of somatotropin administered and the type of delivery system employed. Typically, the greater the amount of somatotropin given, the greater the resulting increase in growth, feed efficiency, lean-fat ratio, lactation, or proliferation of mammary parenchymal cells. Preferably, the dosage varies between 10 to 50 milligrams per animal per day.

The somatotropins of this invention may be administered by known techniques effective for delivery of the desired dose to the animal. These include intramammary, intramuscular or subcutaneous injections, or by the use of controlled release implants. The somatotropins of this invention may be formulated in the same manner as known somatotropins. Such formulations usually include a buffer and an inert carrier.

DESCRIPTION OF PREFERRED EMBODIMENTS

EXAMPLE 1

Preparation of BGH and PGH GLN Variant Genes

The asparagine residues at position 98 of the BGH and PGH structural genes described in Seeburg, P. H. et al., 1983, *DNA* 2:37-45, are changed to glutamine by oligonucleotide-directed, site-specific mutagenesis. Oligonucleotide mutagenesis primers are synthesized on an Applied Biosystems DNA Synthesizer in accordance with the procedures set forth by the manufacturer, Applied Biosystems, Inc. (Foster City, Cal.). The sequence of the mutagenesis primers are:

BGH:
  5'-AAACACCAAGCTCTGGGT-
  GAAGACTCT-3'

PGH:
  5'-AGGGTCTTCACC-
  CAGAGCCTGGTGTTT-3'

The underlining indicates the codon which changes the wild-type asparagine to glutamine.

The BGH gene used as template DNA consisted of the BGH gene described in Seeberg et al. cloned into the M13mp18 vector (Bethseda Research Laboratory, Gaithersburg, Md.) as a EcoRI/HindIII fragment. Also used as a template is the N-alanyl, valine (126) BGH gene described in European Patent Application No. 193,515, published Sep. 3, 1986, cloned into the M13mp18 vector as an EcoRI/HindIII fragment. The PGH gene used as template DNA was the N-alanyl PGH gene described in European Patent Application Number 193,515 cloned into the M13mp19 vector (BRL) as an EcoRI/HindIII fragment. Before the mutagenesis of the N-alanyl PGH gene at position 98, the 5' end of the gene was mutagenized to create an NcoI site in order to facilitate later subcloning into the expression plasmid. The primer used for this mutagenesis was synthesized as those above and has the structure of

PGH:
  5'-CAGTGAATTCTCCATGGCCTTC-
  CCAGC-3'

The mutagenesis procedure for the NcoI site addition is described by Kunkel, *Proc. Natl. Acad. Sci. USA*, 82, 422-492 (1985). All restriction enzymes and modifying enzymes (T4 DNA ligase and polynucleotide kinase) are purchased from New England Biolabs (Beverly, Mass.) and used according to the manufacturer's directions.

The mutagenesis is carried out using the Amersham (Arlington Heights, Ill.) Oligonucleotide-directed in vitro Mutagenesis System, according to instructions of the manufacturer. Following mutagenesis, positive mutant genes are identified by DNA sequence analysis using the Sequenase ™ DNA sequencing system of United States Biochemical Corporation (Cleveland, Ohio) according to the manufacturer's instructions. The mutated genes are then cloned as EcoRI/HindIII fragments into *E. coli* expression vectors pMON2534 for the BGH and N-alanyl BGH genes and pMON5585 for the N-alanyl PGH gene. Plasmid pMON2534 is a derivative of pBGH$_{ex-1}$ (Seeburg et al.) with a tandem lacUV5 promoter inserted at the HindIII site of pB$_{ex-1}$ as a transcription terminator. The sequence of the tandem lacUV5 promoter as an EcoRI fragment is described in Bogosian et al., *Nucleic Acid Research*, 15, 7185. The EcoRI fragment is converted to a HindIII fragment by filling in the EcoRI overhangs and attaching HindIII linkers. These manipulations yield the sequences which are found at the ends of the HindIII fragment. At the upstream end, the HindIII linker (AAGCTT) ligated to the filled in EcoRI end (AATTCT...) produces the sequence AAGCTTAATTCT...; the CT at positions 11 and 12 represents the right half of the AluI site from the original lacUV5 promoter fragment. At the downstream end, the sequence produced is ... AGAAT-TAAGCTT; the AG at positions -12 and -11 represents the left half of the AluI site from the original lacUV5 promoter fragment. In addition, pMON2534 has the EcoRI site at the 5' terminus of the ptrp fragment of pB$_{ex-1}$ and the HindIII site at the 3' terminus of the tandem lacUV5 promoter/operator fragment removed by digestion of the overhang EcoRI and HindIII ends using S1 nuclease and blunt-ended ligation with T$_4$ DNA ligase. Plasmid pMON5585 is a pBR327 plasmid containing E. coli recA promoter, a G10L sequence, and T7 transcription termination sequence as described in European Patent Application Number 241,446, published Oct. 14, 1987. The mutant BGH, N-alanyl BGH and N-alanyl PGH genes cloned into the respective expression plasmids are designated pMON3050, pMON3066 and pMON3299, respectively. The pMON3050 and pMON3066 plasmids are inserted into E. coli strain W3110 (ATCC #39936). pMON3299 is inserted into E. coli strain W3110 which is modified by deletion of fhuA gene by standard procedures (Maniatis et al., eds., 1982, *Molecular Cloning: A Laboratory Manual*, Cold Spring Harbor Laboratory, Cold Spring Harbor, N.Y.).

EXAMPLE 2

Production of BGH and PGH GLN Mutant Proteins

The E. coli cells carrying the pMON3050, pMON3066 or pMON3299 expression plasmids are cultured under conditions which cause expression of the mutant BGH or PGH coding sequences and, hence, production of the mutant BGH or PGH proteins by the transformed E. coli. The growth media for the E. coli and conditions for selection of bacterial cells containing an ampicillin resistance (amp$^r$) marker are as described in Maniatis et al., (1982). When employed for protein expression, E. coli are grown in Luria Broth (LB) or M9 minimal medium (Maniatis et al., 1982) supplemented with 100 µg/ml ampicillin. Induction of transcription from the recA promoter in pMON3299 is conducted as follows. Overnight cultures of E. coli host cells carrying expression plasmids are diluted to 20-25 Klett units (measured with a Klett-Summerson meter using a green filter, Klett Mfg. Co., New York, N.Y.) in M9 minimal media supplemented with 0.25% (w/v) glucose and 1% (w/v) casamino acids and 0.25% µg/ml thiamine and grown to a cell density of 150–180 Klett units. The cells are then induced by addition of nalidixic acid to the growth media at a final concentration of 50 µg/ml. Growth is continued for several hours at 37° C. with aliquots taken at 2 or 3 hours after induction for heterologous protein analysis. A high level of aeration is maintained throughout the growth in order to achieve maximal production of the desired gene product. Induction of transcription from the ptrp promoter in pMON3050 and pMON3066 is as described in Seeburg et al., 1983, and Calcott et al., 1988, *Developments in Industrial Microbiology* 29, 257–266.

Following production in E. coli, the mutant BGH and PGH proteins are purified as follows using reagents purchased from Sigma (St. Louis, Mo.) unless otherwise noted. The recombinant E. coli cells are homogenized using an Ultra-Turrax (Tekmar Co., Cincinnati, Ohio). The cells are then lysed by passage through a precooled Manton Gaulin (APV Gaulin, Everett, Mass.) three times at 258,263–332,053 newton/m$^2$ and then centrifuged at 25,000 rpm for 20 minutes at 4° C. The isolated pellets are rinsed and homogenized as previously described and urea added to a final concentration of 4.5M urea. The PGH mixture also contains 90 mM Tris base. The pH is then adjusted to 11.3 with NaOH and the BGH and PGH protein allowed to fold for about 2½ days at 4° C. while stirring. The mixture is centrifuged at 25,000 rpm for 30 minutes at 4° C. to remove any remaining precipitate. The BGH and PGH mutant proteins are then separated from E. coli contaminants using DE-52 chromatography. The GH proteins are eluted from the column with an HCl conductivity gradient between 350 and 1000µ Semens/cm. Fractions containing the purified mutant BGH and PGH proteins (determined by HPLC on a C-8 column, Alltech Assoc., Deerfield, Ill., eluted with a gradient of 50–65% [v/v] acetonitrile containign 0.1% [v/v] TFA) and pooled and concentrated over YM10 membranes in a stirred cell apparatus, Amicon, Danvers, Mass.

The BGH Gln mutants proteins are dialyzed versus 4 changes of 25 mM NaHCO$_3$, pH10, followed by 4 changes of water prior to lyophilization on a Virtis Freezemobile 24 (Gardiner, N.Y.).

The PGH Gln mutant protein is dialyzed versus 4 changes of 5 mM NaHCO$_3$, pH10, prior to lyophilization. Lyophilized proteins are stored at −20° C. prior to assay.

Assays, specifically, in vitro liver radio-receptor assay using the method of Haro et al., *Mol. Cell. Endocrinol.*, 38, 109–116 (1984) and in vitro assay for measuring the inhibition of insulin-stimulated $C^{14}$-glucose incorporation into lipids by the method of Glenn et al., *J. Cell. Biochem.* 37, 371–383 (1988) indicate that the Gln98 somatotropins of this invention exhibit essentially equivalent biological activity as the corresponding unmutated somatotropins.

In vivo test in rats using a weight gain assay also shows essentially equivalent biological activity for the Gln98 somatotropins of this invention.

EXAMPLE 3

Stability of Gln Mutant Proteins

Solution stability of somatotropins are evaluated at pH10 and 11 for periods of 3 and 7 days. Specimens are prepared by dissolving 2 mg/ml of a test somatotropin in 25 millimolar NaHCO$_2$, at the desired pH, at 22° C. The pH is adjusted to 10 or 11 by adding 2.5 molar NaOH. The specimens are held at 22° C. and samples are analyzed initially and after 3 and 7 days by reverse phase high performance liquid chromatography. The results obtained at pH10 and pH11 are tabulated in Tables 2 and 3, respectively. The data are reported as area percent. Non detectable amounts are indicated by nd. Peak 1 indicates the quantity of the two-chain form of the somatotropin which has been cleaved at asparagine 98. Peak 2 indicates the quantity of beta-linked aspartic acid somatotropin at residue 98. The composition of Peak 3 is unknown. Both the BGH and BGH-Gln98 somatotropins have a methionine at position -1. Both the PGH and PGH-Gln98 somatotropins have an alanine at -1.

TABLE 2

| | Stability at pH 10 | | |
|---|---|---|---|
| | Time (days) | Peak 1 % | Peak 2 % | Peak 3 % |
| BGH | 0 | nd | nd | nd |
| BGH-Gln98 | 0 | nd | nd | 0.8 |
| BGH | 3 | 0.8 | 3.8 | 0.9 |
| BGH-Gln98 | 3 | nd | nd | 0.7 |
| BGH | 7 | 1.8 | 8.3 | 3.1 |
| BGH-Gln98 | 7 | nd | nd | nd |
| PGH | 0 | nd | 1.6 | nd |
| PGH-Gln98 | 0 | nd | nd | nd |
| PGH | 3 | 0.8 | 5.4 | 1.4 |
| PGH-Gln98 | 3 | nd | nd | nd |
| PGH | 7 | 1.7 | 9.7 | 2.3 |
| PGH-Gln98 | 7 | nd | nd | 1.0 |

TABLE 3

| | Stability at pH 11 | | | |
|---|---|---|---|---|
| | Time (days) | Peak 1 % | Peak 2 % | Peak 3 % |
| BGH | 0 | nd | nd | nd |
| BGH-Gln98 | 0 | nd | nd | 0.7 |
| BGH | 3 | 1.8 | 7.6 | nd |
| BGH-Gln98 | 3 | nd | nd | 1.8 |
| BGH | 7 | 4.7 | 18.8 | 8.6 |
| BGH-Gln98 | 7 | nd | nd | 3.0 |
| PGH | 0 | nd | 1.7 | nd |
| PGH-Gln98 | 0 | nd | nd | nd |
| PGH | 3 | 2.8 | 10.1 | 3.7 |
| PGH-Gln98 | 3 | nd | nd | 0.7 |
| PGH | 7 | 5.1 | 17.2 | 5.4 |
| PGH-Gln98 | 7 | nd | nd | 1.4 |

The data show that normal somatotropins are unstable at high pH with significant amounts of two-chain and beta-linked by-products forming over time, whereas, the data show that the GLn98 somatotropins are stable with no detectable amounts of the two-chain or beta-linked by-products formed.

Although the invention has been illustrated by typical examples, it is not limited thereto. Changes and modifications of the examples of the invention herein chosen for purposes of disclosure can be made which do not constitute departure from the spirit and scope of the invention.

We claim:

1. A DNA molecule with the sequence coding for a mammalian somatotropin in which the codon for asparagine located at position 98 or 99 of somatotropin is replaced by a codon for glutamine.

2. The DNA molecule with the sequence of claim 1 in which the somatotropin is a bovine somatotropin.

3. The DNA molecule with the sequence of claim 2 which codes for glutamine at position 98.

4. The DNA molecule with the sequence of claim 3 which codes for methionine and phenylalanine at positions minus one and one, respectively.

5. The DNA molecule with the sequence of claim 3 which codes for alanine and phenylalanine at positions minus one and one, respectively.

6. The DNA molecule with the sequence of claim 5 which codes for valine at position 126.

7. The DNA molecule with the sequence of claim 1 in which the somatotropin is a porcine somatotropin.

8. The DNA molecule with the sequence of claim 7 which codes for glutamine at position 98.

9. The DNA molecule with the sequence of claim 8 which codes for alanine and phenylalanine at positions minus one and one, respectively.

10. The DNA molecule with the sequence of claim 1 in which the codon for glutamine is CAA.

11. The DNA molecule with the sequence of claim 1 in which the codon for glutamine is CAG.

* * * * *